United States Patent [19]

Meilland

[11] Plant 4,912

[45] Nov. 2, 1982

[54] ROSE PLANT—MEITOFLAPO VARIETY

[75] Inventor: Marie L. Meilland, Antibes, France

[73] Assignee: The Conrad-Pyle Company, West Grove, Pa.

[21] Appl. No.: 235,918

[22] Filed: Feb. 19, 1981

[51] Int. Cl.[3] ..... A01H 5/00

[52] U.S. Cl. ..... Plt./26

[58] Field of Search ..... Plt./18, 26

*Primary Examiner*—Robert E. Bagwill

*Attorney, Agent, or Firm*—Burns, Doane, Swecker & Mathis

[57] ABSTRACT

A new rose plant of the Floribunda Class is provided having attractive double flowers which are china pink on the inside and neyron pink on the outside. Such flowers are formed in abundance and when cut are long lasting. The plant is particularly susceptible to forcing.

17 Drawing Figures

SUMMARY OF THE INVENTION

The object of the present invention is to provide a new variety of rose plant of the Floribunda Class which is distinguished from prior varieties by the following characteristics:

(1) from the physical point of view, the rose plant with bronze green mature wood has a semi-erect growth habit, double flowers which are china pink on the inside and neyron pink on the outside, and consistent petals which bear a whitish unguis on both surfaces, and (2) from the biological point of view, the rose plant has vigorous vegetation, produces flowers in abundance, exhibits an ability readily to be forced, is not particularly susceptible to diseases, and forms long lasting flowers comprising petals which detach cleanly.

In view of these characteristics the new variety meets the needs of the horticultural industry for all uses, and particularly is suited for the production of long lasting cut flowers.

The new variety was created by artificial pollination whereby two parents which previously had been studied for the possession of the characteristics sought in the new variety were produced and combined.

The seed parent of the new variety resulted from the crossing of the Jack Frost variety (U.S. Plant Pat. No. 2,447) with an unnamed variety formed by the crossing of the Meialfi variety with an unnamed variety formed by the crossing of the Meger variety and the Meban variety.

The pollen parent of the new variety resulted from the crossing of the Meialfi variety with an unnamed variety formed by the crossing of the Meger variety and the Meban variety with the product being crossed by another unnamed variety.

The parentage of the new variety may be expressed as follows:

[Jack Frost × [Meialfi × (Meger × Meban)]] × [[Meialfi × (Meger × Meban)] × Unnamed Variety]

The seeds resulting from the above pollination were sown and 141 plantlets were obtained which were physically and biologically different from each other. Selective study resulted in the identification of a single plant of the new variety. Extensive testing has confirmed the behavior and characteristics of the new variety which is particularly suited for the abundant production of long lasting cut flowers having a distinctive coloration.

The characteristics and properties of the new variety have been found to be transmissible by agamic means, also called "asexual", i.e., by means of vegetative propagation, in particular by grafting an eye. The rose plant of the new variety has been designated the MEITOFLAPO variety.

BRIEF DESCRIPTION OF THE PHOTOGRAPH

The accompanying photograph shows typical specimens of the cut flowers and foliage of the present variety when grown under glass at Antibes, France as nearly true as it is reasonably possible to make the same in a color illustration of this character, illustrated in:

FIG. 1—a specimen of young shoot;

FIG. 2—a specimen of a bud at the opening of the sepals;

FIG. 3—a specimen of a bud at the opening of the petals;

FIG. 4—a specimen of a flower in the course of opening;

FIG. 5—a specimen of an open flower—plan view—obverse;

FIG. 6—a specimen of an open flower—plan view—reverse;

FIG. 7—a specimen of a flower in full bloom—plan view —obverse;

FIG. 8—a specimen of a flower in full bloom—plan view—reverse;

FIG. 9—a specimen of fruit;

FIG. 10—a specimen of a receptacle showing the arrangement of the stamens;

FIG. 11—a specimen of a receptacle showing the arrangement of the pistils (sepals and stamens removed);

FIG. 12—a specimen of a flowering stem;

FIG. 13—a specimen of a main branch;

FIG. 14—a specimen of leaf with 3 leaflets, upper surface;

FIG. 15—a specimen of leaf with 5 leaflets, upper surface;

FIG. 16—a specimen of leaf with 7 leaflets, upper surface; and

FIG. 17—a specimen of leaf with 9 leaflets, under surface.

DETAILED DESCRIPTION

Figures 1, 2, 3, 4, 5, 6, 7, 8, 9, 10, 11, 12, 13, 14, 15, 16, 17:
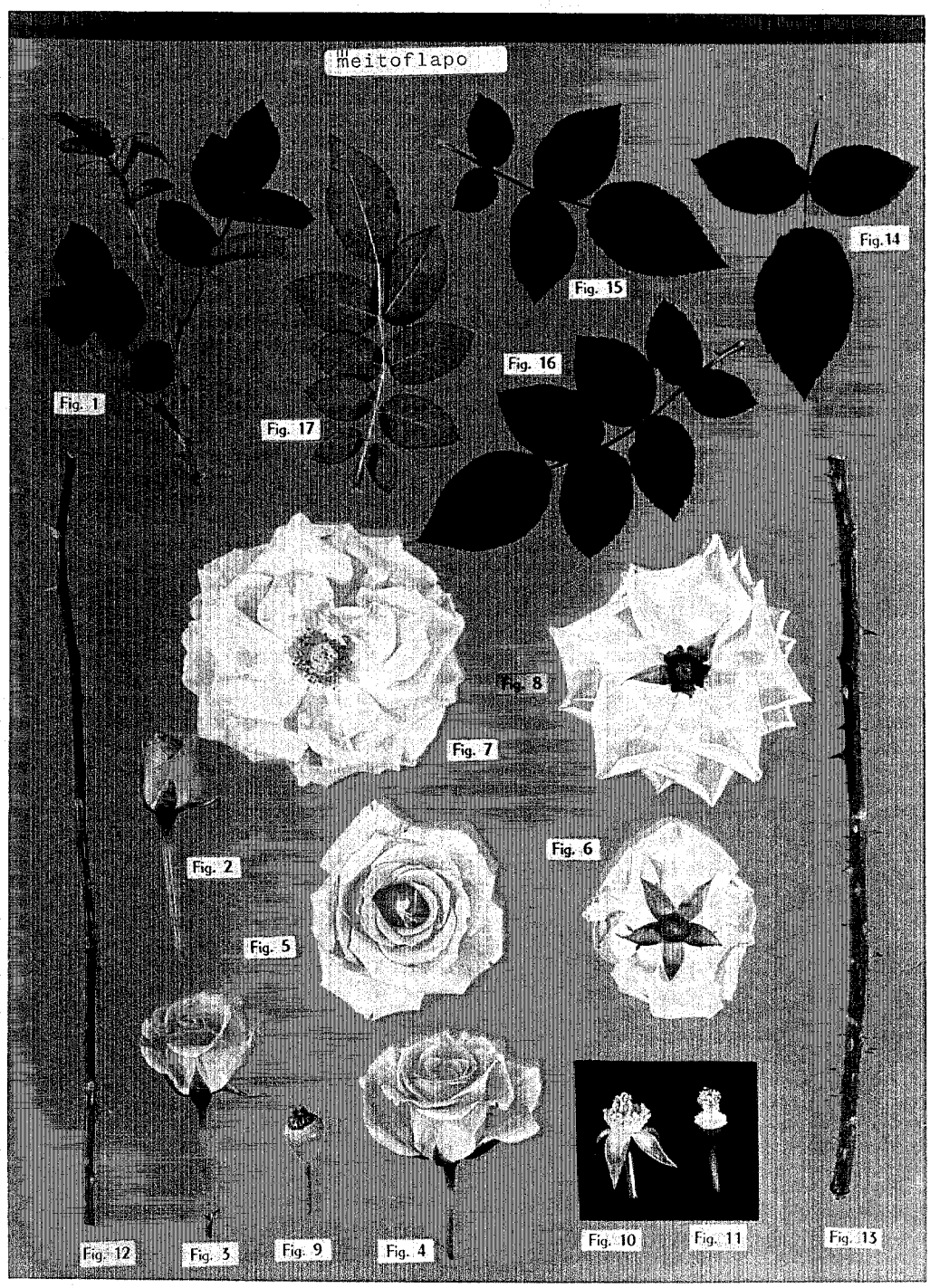

The plant described was grown under glass at Antibes, France.

The chart utilized in the identification of the colors is that of the Royal Horticultural Society (R.H.S. Colour Chart). The terminology preceding the numbered references to this chart has been added to designate in common terms the corresponding colors.

Class: Floribunda.

Plant:

*Height.*—On the basis of the cutting back of the plants in greenhouses to approximately 0.85 m., the length of the cut flower bearing stems reaches approximately 40 to 45 cm.

*Bearing.*—Semi-erect.

Branches:

*Color.*—Young stems: bronze green 146/A (yellow green group) with very slightly shaded reddish coloration. Mature wood: bronze green 146/A (yellow green group).

*Prickles.*—Shape — upper edge: slightly convex. Under edge: concave. Size: small. Quantity: moderately numerous. Color on young stems: initially reddish, then they become greenish. Color on mature wood: havana brown.

Leaves:

*Stipules.*—Adnate, pectinate, fairly narrow and linear.

*Petioles.*—Inner surface: grooved, reddish brown (young foliage) and green (adult foliage) with more or less glandular edges. Outer surface: light green with a few small hooked prickles.

*Folioles.*—Number: 3 or 5 or 7, and occasionally 9. Shape: oval base with lanceolate top. Teeth: simple and regular. Texture: leathery. General effect: small foliage, dense and semi-dull.

*Color.*—Young foliage: upper surface: dark green 147/A (yellow green group). Under surface: medium green 147/B (yellow green group). Adult foliage: upper surface: bronze green 146/A (yellow green group). Under surface: light green 147/C (yellow green group).

Inflorescence:

*Number of flowers.*—Generally one flower per stem when grown in forced culture under glass, however in such forced culture the first axillary eye below the flower sometimes develops. When grown outside in the landscape multiple flowers per stem are produced.

*Penduncle.*—Erect, rigid, light green, very slightly glandular. The length is approximately 5 cm. on the average.

*Sepals.*—Upper surface: tomentous, greenish. Under surface: light green, very slightly glandular. The outer sepals have their edges slightly glandular and have a few appendages.

*Bud.*—Shape: before the opening of the sepals it is conical. Length: approximately 3 cm. on average outside the calyx at the opening of the sepals. Size: medium. Color when opening: upper surface: carmine pink 52/C (red group). Under surface: neyron pink 55/A (red group).

*Flower.*—Shape: initially with parallel sides and subsequently in the form of a hollow cup, double flower. Diameter: approximately 8 to 10 cm. on the average. Color: when first opening: inside: china pink 58/D (red purple group). During the course of opening fully: inside: china pink 58/D (red purple group). Outside: neyron pink 55/D (red group). Fragrance: none. Lasting quality: very long when cut. Corolla: petals: texture: firm. Shape: rounded shape becoming more ovoid towards the center. The top commonly possesses a small point. The unguis is whitish on both surfaces. Number: approximately 25 on the average. Shedding petals: the petals drop off cleanly. Stamens: number: approximately 136 on the average. Anthers: ocher colored. Filaments: whitish and irregular. Pistils: number: 60 on average. Stigmas: yellow. Styles: twisted, whitish and fuschine at top. Receptacle: light green at dehiscence of the anthers, and in longitudinal section it is narrow and in the shape of a jug.

Development:

*Vegetation.*—Vigorous.

*Flowering.*—Very high.

*Aptitude for forcing.*—Excellent.

*Resistance to diseases.*—Good.

It should be emphasized that the plants of the new variety described herein were grown under glass to produce cut flowers, and that when such new variety is grown out-of-doors it commonly exhibits typical Floribunda characteristics such as multiple buds per stem.

I claim:

1. A new and distinct variety of Floribunda rose plant of vegetative reproduction substantially as illustrated and described characterized by the fact that from the physical point of view, the rose plant with bronze green mature wood has a semi-erect growth habit, double flowers which are china pink on the inside and neyron pink on the outside, and consistent petals which bear a whitish unguis on both surfaces; and from the biological point of view, the rose plant has vigorous vegetation, produces flowers in abundance, exhibits an ability readily to be forced, is not particularly susceptible to diseases, and forms long lasting flowers comprising petals which detach cleanly.

* * * * * meitoflapo